United States Patent
Thompson et al.

(10) Patent No.: US 9,211,355 B2
(45) Date of Patent: Dec. 15, 2015

(54) SCENT WARMERS HAVING NON-INCANDESCENT HEATING AND LIGHT-EMITTING DEVICES AND RELATED METHODS

(75) Inventors: R. Orville Thompson, Eagle, ID (US); Xiao Mingren, Miaoli County (TW)

(73) Assignee: Scentsy, Inc., Meridian, ID (US)

( * ) Notice: Subject to any disclaimer, the term of this patent is extended or adjusted under 35 U.S.C. 154(b) by 0 days.

(21) Appl. No.: 13/092,697

(22) Filed: Apr. 22, 2011

(65) Prior Publication Data
US 2012/0024837 A1    Feb. 2, 2012

Related U.S. Application Data

(60) Provisional application No. 61/368,181, filed on Jul. 27, 2010.

(51) Int. Cl.
*B01D 1/00* (2006.01)
*A61L 9/03* (2006.01)
*F27D 11/00* (2006.01)

(52) U.S. Cl.
CPC .............. *A61L 9/03* (2013.01); *Y10T 29/49083* (2015.01)

(58) Field of Classification Search
CPC ..... A61L 9/035; A61L 2209/12; F21S 8/035; H01R 33/22; H01L 23/345; F22B 1/282
USPC ................. 392/390–5, 386, 438, 429, 432–3; 219/433; 239/34–5; 422/5, 125
See application file for complete search history.

(56) References Cited

U.S. PATENT DOCUMENTS

| | | |
|---|---|---|
| 5,651,942 A | 7/1997 | Christensen |
| 5,903,710 A | 5/1999 | Wefler et al. |
| 5,945,094 A | 8/1999 | Martin et al. |
| 6,085,026 A | 7/2000 | Hammons et al. |
| 6,106,786 A | 8/2000 | Akahoshi |
| 6,354,710 B1 | 3/2002 | Nacouzi |
| 6,478,440 B1 | 11/2002 | Jaworski et al. |
| 6,627,857 B1 | 9/2003 | Tanner et al. |

(Continued)

FOREIGN PATENT DOCUMENTS

| | | | |
|---|---|---|---|
| CN | 201304124 | | 9/2009 |
| CN | 201510547 | * | 6/2010 |

(Continued)

OTHER PUBLICATIONS

Letter dated Nov. 18, 2013 from Lynn G. Foster to J. Jeffrey Gunn and Stephen E. Pulley with Enclosures; Candle Warmer "The original alternative to lighting a candle" Product Guide 2005, www.candlewarmers.com, 4 pages.*

(Continued)

*Primary Examiner* — Shawntina Fuqua
(74) *Attorney, Agent, or Firm* — TraskBritt (57) ABSTRACT

A scent warmer has a base structure including a lower portion and a scented material-holding portion. The lower portion may include at least one sidewall and be at least substantially hollow. An electrical heat source and a filamentless electrical light source may be disposed in the base structure lower portion. The scent warmer may include a power supply input element for providing electrical power to the electrical heat source and the filamentless electrical light source. Methods of the invention may include methods of warming a scented material and methods of forming a scent warmer.

25 Claims, 4 Drawing Sheets

(56) References Cited

U.S. PATENT DOCUMENTS

| | | |
|---|---|---|
| 6,779,905 B1 | 8/2004 | Mazursky et al. |
| 6,805,300 B2 | 10/2004 | Munroe et al. |
| 6,917,754 B2 | 7/2005 | Pedrotti et al. |
| 6,966,665 B2 | 11/2005 | Limburg et al. |
| 7,046,919 B2 * | 5/2006 | Shimizu et al. ............... 392/390 |
| 7,121,686 B1 | 10/2006 | Chu |
| 7,186,016 B2 | 3/2007 | Jao |
| 7,246,919 B2 | 7/2007 | Porchia et al. |
| 7,277,626 B2 | 10/2007 | Pesu et al. |
| 7,318,659 B2 | 1/2008 | Demarest et al. |
| 7,350,720 B2 | 4/2008 | Jaworski et al. |
| 7,419,281 B2 | 9/2008 | Porchia et al. |
| 7,455,444 B2 | 11/2008 | Chien |
| 7,476,002 B2 | 1/2009 | Wolf et al. |
| 7,481,571 B2 | 1/2009 | Bistritzky et al. |
| 7,484,860 B2 | 2/2009 | Demarest et al. |
| 7,503,668 B2 | 3/2009 | Porchia et al. |
| 7,503,675 B2 | 3/2009 | Demarest et al. |
| 7,543,957 B1 | 6/2009 | Balazs et al. |
| 7,572,412 B2 | 8/2009 | Yang |
| 7,611,253 B2 | 11/2009 | Chien |
| 7,618,151 B2 | 11/2009 | Abbondanzio et al. |
| 7,641,364 B2 | 1/2010 | Abbondanzio et al. |
| 7,687,744 B2 | 3/2010 | Walter et al. |
| 7,699,603 B2 | 4/2010 | Furner et al. |
| 7,824,627 B2 | 11/2010 | Michaels et al. |
| 7,839,068 B2 | 11/2010 | Hayashi et al. |
| 7,932,482 B2 | 4/2011 | Norwood et al. |
| 2005/0016985 A1 | 1/2005 | Haas et al. |
| 2005/0184045 A1 | 8/2005 | Shimizu et al. |
| 2005/0195600 A1 | 9/2005 | Porchia et al. |
| 2006/0152946 A1 | 7/2006 | Chien |
| 2007/0086199 A1 | 4/2007 | Demarest et al. |
| 2008/0279731 A1 | 11/2008 | Goreham et al. |
| 2009/0025567 A1 | 1/2009 | Greenberg et al. |
| 2009/0073694 A1 | 3/2009 | Scannell, Jr. |
| 2009/0196587 A1 | 8/2009 | Cheung |
| 2009/0289047 A1 | 11/2009 | Hisao |
| 2010/0096376 A1 | 4/2010 | Hsiao |
| 2010/0260646 A1 | 10/2010 | Jorgensen |
| 2010/0270943 A1 | 10/2010 | Cook |
| 2010/0290254 A1 | 11/2010 | Howard et al. |
| 2011/0110092 A1 | 5/2011 | Hsiao |
| 2011/0110118 A1 | 5/2011 | Hsiao |
| 2011/0110824 A1 | 5/2011 | Hsiao |
| 2012/0024837 A1 | 2/2012 | Thompson |

FOREIGN PATENT DOCUMENTS

| | | |
|---|---|---|
| DE | 20 2009 005303 | 7/2009 |
| DE | 20 2009 014766 | 2/2010 |
| EP | 0884078 | 12/1998 |
| JP | 11-197226 | 7/1999 |
| JP | 2001-327588 | 11/2001 |
| JP | 2003-310732 | 11/2003 |
| JP | 3146210 U9 | 10/2008 |
| WO | WO2005-074999 | 8/2005 |
| WO | WO2009027668 | 3/2009 |
| WO | WO2009027670 | 3/2009 |
| WO | WO2010062529 | 6/2010 |
| WO | WO2010135789 | 12/2010 |

OTHER PUBLICATIONS

Brandon Juarez, U.S. Appl. No. 13/160,790, filed Jun. 15, 2011.
Brandon Juarez, U.S. Appl. No. 13/160,842, filed Jun. 15, 2011.
Extended European Search Report for EP application 11164677.4 dated Sep. 19, 2011, 5 pages.
International Search Report for PCT/US2011/033629, dated Dec. 29, 2011.
Written Opinion for PCT/US2011/033629, dated Dec. 29, 2011.
European Search Report for EP Application No. 11164677.4 dated Sep. 19, 2011.
Letter Dated Nov. 18, 2013 from Lynn G. Foster to J. Jeffrey Gunn and Stephen E. Pulley with Enclosures; Candle Warmer "The original alternative to lighting a candle" Product Guide 2005, www.candlewarmers.com, 4 pages; color photograph.
Search Report from Singapore Patent Office for application No. 201300632-5, dated Apr. 9, 2014.
Examination Report for AU application No. 2011286420, dated Mar. 6, 2015, 4 pages.

* cited by examiner

SCENT WARMERS HAVING NON-INCANDESCENT HEATING AND LIGHT-EMITTING DEVICES AND RELATED METHODS

CROSS-REFERENCE TO RELATED APPLICATION

This application claims the benefit of U.S. Provisional Patent Application Ser. No. 61/368,181, filed Jul. 27, 2010, entitled "Scent Warmers Having Non-candescent Heating and Light Emitting Devices and Related Methods," the disclosure of which is incorporated herein by reference in its entirety.

TECHNICAL FIELD

Embodiments of the present invention relate generally to scent warmers, methods of forming scent warmers, and methods of warming a scented material.

BACKGROUND

For many years, candles made from scented wax have been used to create an aroma in surrounding area. Traditionally, candles include a wick that may be lit by a flame. The burning wick melts the wax near the wick and pulls the liquid wax, along with the scents included in the wax, up into the wick by capillary action or absorption. The flame burns the scented wax, and an aroma is released into the area surrounding the candle. The flame of the traditional candle also produces light, which is often regarded as desirable for creating a pleasing ambience or for providing energy efficient light, for example. While light and an aroma are produced by candles, traditional candles produce some risks and hazards, including a risk of burns, fires, and smoke.

Recently, scent warmers have been used, as an alternative to candles, to heat scented wax or scented oil. Scent warmers are often referred to as flameless candles or wickless candles. Some scent warmers release the aroma from the scented wax or oil without the use of a flame. For example, scent warmers may include a base that houses an incandescent light bulb acting as a heat source. The incandescent light bulb is positioned inside the base under a plate holding the scented wax or oil. The incandescent light bulb heats the bottom of the plate primarily through radiation and convection. The plate, in turn, heats the wax or oil, thus releasing the scent into the surrounding area by increasing the rate of evaporation or dissipation of the scented material. Such scent warmers are generally safer than traditional candles because of the absence of a flame. However, incandescent light bulbs are generally seen as inefficient and may include their own disadvantages. For example, incandescent bulbs may need frequent replacement, adding to the cost of operating the scent warmer.

Other scent warmers use a resistive heating element, rather than an incandescent light bulb, to heat scented wax or oil. Such scent warmers may include a plate for holding scented wax or oil with a resistive heating element attached to the bottom of the plate. The heating element heats the plate primarily by conduction, and the plate transfers the heat to the scented wax or oil, thereby releasing an aroma into the surrounding area. However, these scent warmers do not produce light.

It is desirable to create an improved scent warmer that embodies the benefits of traditional candles and scent warmers while minimizing the drawbacks of their various designs.

BRIEF SUMMARY

In some embodiments, scent warmers may include a base structure with an at least substantially hollow lower portion, the lower portion having at least one sidewall. A scented material-holding portion may be disposed over the lower portion. An electrical heat source may be disposed at least partially within the lower portion and positioned proximate the scented material-holding portion. Furthermore, a filamentless electrical light source may also be disposed at least partially within the lower portion. Optionally, the invention may also include additional circuitry, a heat plate located between the scented material-holding portion and the electrical heat source, structural components, or combinations thereof.

In other embodiments, methods of warming a scented material may include thermally coupling an electrical heat source with a plate having scented material disposed at least partially thereon, heating the plate by providing electrical power to the electrical heat source, and producing light by providing electrical power to a filamentless electrical light source disposed at least partially within a base structure. Optionally, the invention may further include allowing at least some light to pass through the base structure by, for example, forming at least a portion of a sidewall of the base structure to exhibit less than 100% opacity, forming at least one hole in the sidewall of the base structure, or a combination thereof. Such methods may also include causing light produced by the filamentless electrical light source to flicker.

In additional embodiments, methods of forming a scent warmer may include electrically connecting a power supply input element to a filamentless electrical light source and to an electrical heat source, coupling the electrical heat source to a plate of a base structure, disposing the filamentless electrical light source at least partially within a lower portion of the base structure, and disposing a scented material-holding portion proximate the electrical heat source. Embodiments may also include forming at least one hole through the lower portion of the base structure, selecting a material of the lower portion of the base structure to exhibit less than 100% opacity, or combinations thereof.

DETAILED DESCRIPTION

The illustrations presented herein are not meant to be actual views of any particular material, apparatus, system, or method, but are merely idealized representations, which are employed to describe certain embodiments of the present invention. For clarity in description, various features and elements common among the embodiments of the invention may be referenced with the same or similar reference numerals.

As used herein, any directional term (e.g., upper, lower, side, top, bottom, etc.) refers to a direction relative to the device when the device is used during normal operation. By way of non-limiting example, an upper portion of a scent warmer is the upper portion while the scent warmer is placed on a surface in an orientation for use, and used to warm scented material.

Figure 1:
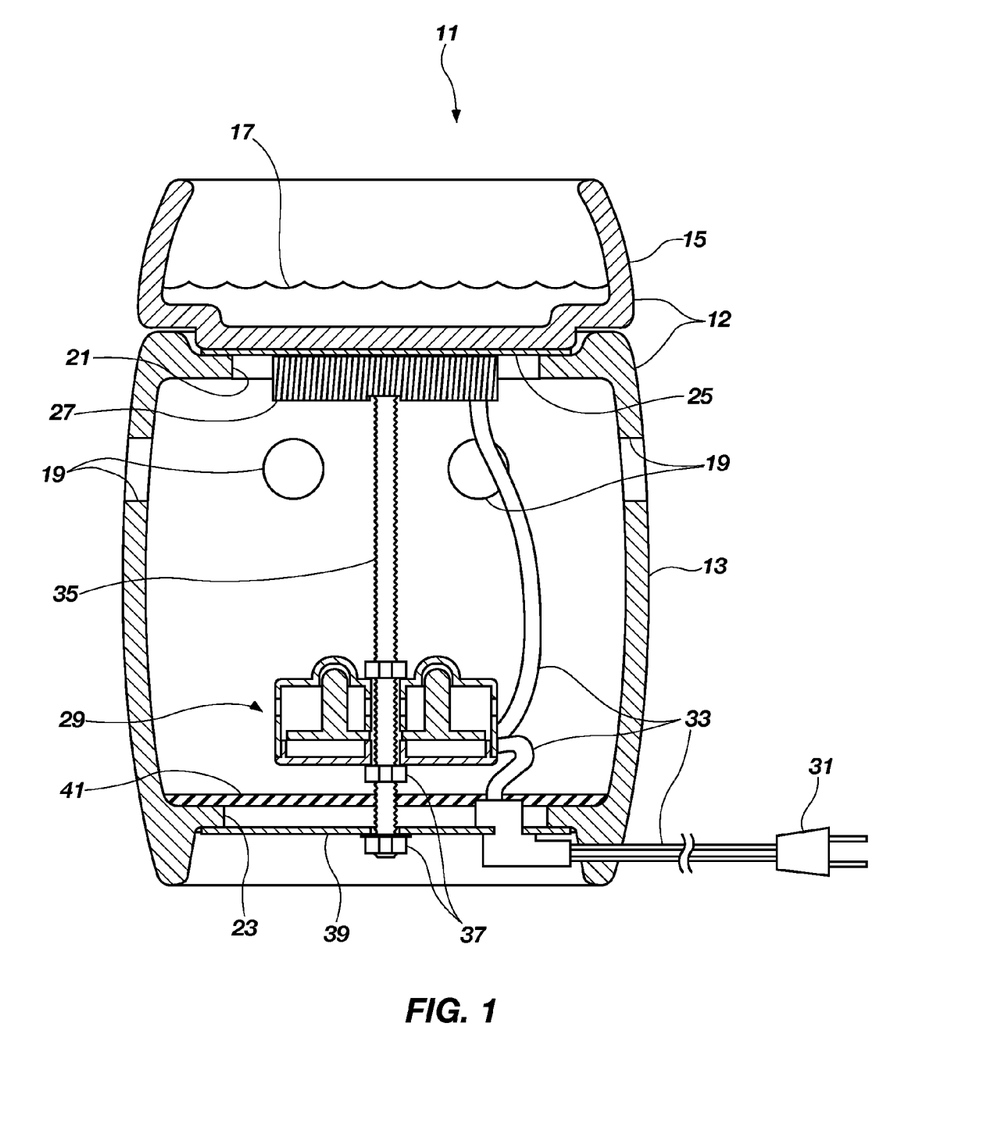
FIG. 1 is a cross-sectional side view of a scent warmer according to an embodiment of the present invention.

FIG. 1 is a cross-sectional side view of a scent warmer 11 according to an embodiment of the present invention. The scent warmer 11 may include a base structure 12, which includes a base structure lower portion 13 and a scented material-holding portion 15 coupled to the base structure lower portion 13. The base structure lower portion 13 may be at least substantially hollow, in that a cavity is defined therein. The scent warmer 11 further includes an electrical heat source 27 and a filamentless electrical light source 29 disposed within the base structure lower portion 13. In some embodiments, the electrical heat source 27 may be coupled with a heat plate 25. Some embodiments may also include a power supply connection 31, an electrical switch (not shown), holes 19 in the base structure lower portion 13, and scented material 17 at least partially disposed within or on the scented material-holding portion 15. Each of the foregoing components, along with the other components having numerical designations shown in FIG. 1, will be described in more detail hereinafter.

In some embodiments, the scented material 17 to be warmed by the scent warmer 11 may include, for example, a scented wax, a scented oil, a scented water, perfume, potpourri, spices, or a combination thereof. While the scented material 17 is generally represented in FIG. 1 as a liquid material, it is contemplated that the scented material 17 may be in liquid, gel, or solid form. Therefore, any scented material 17 that may be caused to release a stronger scent or aroma into a surrounding area upon being heated may be used with the scent warmer 11.

Figure 2:
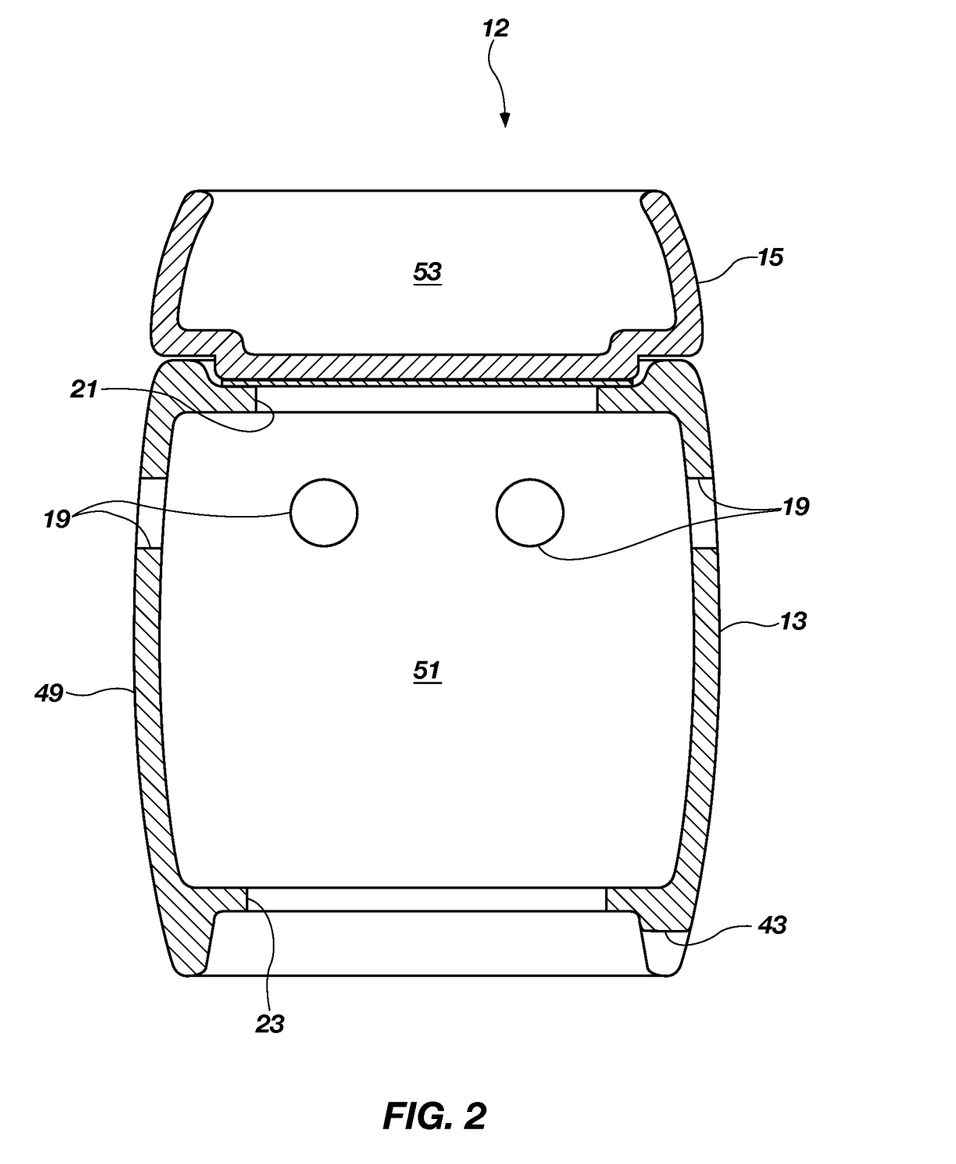
FIG. 2 is a cross-sectional side view of a base structure of the scent warmer of FIG. 1.

FIG. 2 is a cross-sectional side view of the base structure 12 of the scent warmer 11 of FIG. 1. The base structure 12 may include a base structure lower portion 13 and a scented material-holding portion 15. The base structure lower portion may be at least substantially hollow, in that a cavity is defined therein, to house the electrical heat source 27 (FIG. 1) and the electrical light source 29 (FIG. 1). The base structure lower portion 13 and scented material-holding portion 15 may be any desirable shape, such as, for example, generally cylindrical, box-shaped, bulbous, irregular, or any combination of such shapes. The shape and size of the base structure 12 of the scent warmer 11 may be chosen for a variety of reasons. For example, the size and shape of the base structure 12 may be chosen to: improve the aesthetic appeal of the scent warmer; reduce costs of manufacture, packaging, and shipping; provide stability for the placement of the base structure 12 on a horizontal surface, attachment to a vertical surface (e.g., being plugged into a wall outlet), or interfacing with other surfaces or methods of display; and allow consumers a choice of a variety of shapes and sizes to fit their needs or desires, among other contemplated reasons.

The base structure 12 may be formed by methods known to those of ordinary skill in the art out of, by way of non-limiting examples, a ceramic material (e.g., porcelain, clay, glass, etc.), a polymer material (e.g., plastic), wood, metal, or any combination thereof. The base structure 12 may optionally include artistic decorations in the base structure 12 or on or on, or in any surface of the base structure 12. For example, the base structure 12 may be decorated with paint, glaze, artistic designs, carvings, cutouts, pictures, patterns, inserts, attachments, or any combination thereof.

With continued reference to FIG. 2, some embodiments include a sidewall 49 of the base structure lower portion 13 optionally including at least one hole 19 formed therethrough. The at least one hole 19 may allow light from an interior 51 of the base structure lower portion 13 to be visible through the at least one hole 19. Additionally, the at least one hole 19 may facilitate cooling of the base structure 12 as heated air builds up within the base structure lower portion 13 as the scent warmer 11 is used. The at least one hole 19 may be any desired shape and size for aesthetics, cooling, and light passage. For example and without limitation, the at least one hole 19 may be circular (as shown in FIG. 2), triangular, rectangular, polygonal, star-shaped, crescent-shaped, irregularly shaped irregularly shaped, flower-shaped, etc. Furthermore, in some embodiments, the sidewall 49 may have a plurality of holes 19 therethrough, as shown by way of example in FIG. 2. The hole 19 or plurality of holes 19 may be formed during or after the fabrication of the base structure 12 by stamping, drilling, forming a mold with a complementary feature, or any other suitable method, as will be appreciated by one of ordinary skill in the art.

In some embodiments, the base structure lower portion 13 may, optionally, include an upper opening 21 and a lower opening 23 through a respective top and bottom of the base structure lower portion 13. The upper opening 21 may be configured to enable positioning of at least a portion of an electrical heat source 27 (FIG. 1) therein or therethrough. The lower opening 23 may be configured to allow at least partial passage of electrical and structural components, such as, for example, a filamentless light source 29, an electrical heat source 27, a screw 35, an electrical cord 33, and other components, each of which are shown in FIG. 1 and will be more fully described hereinafter. The upper opening 21 and the lower opening 23 may each be sized and configured to allow access to the components for installation, repair, maintenance, replacement, etc. Additionally, in some embodiments, a recess 43 may be cut out or otherwise formed in the sidewall 49 to allow a power supply input element in the form of an electrical cord 33 to pass through the recess 43 (as shown in FIG. 1). The recess 43 may also comprise a hole, slot, or other passage configured to allow an electrical cord therethrough and may be placed at any convenient location in the sidewall 49. For example, the recess 43 may be positioned proximate the bottom of the sidewall 49, as shown in FIG. 2.

The scented material-holding portion 15 of the base structure 12 may be formed to be at least partially concave, as shown in FIGS. 1 and 2, or otherwise configured, to hold scented material 17 therein during use. In other words, the scented material-holding portion 15 may form a scented material receptacle 53. The scented material-holding portion 15 may be referred to as a "plate". In some embodiments, the scented material-holding portion 15 may be formed separately from the base structure lower portion 13, as shown in FIG. 2. In such embodiments, a bottom surface of scented material-holding portion 15 may be complementarily shaped and sized relative to a top of the base structure lower portion 13, so that the scented material-holding portion 15 may be placed and maintained on top of the base structure lower portion 13 in a normal operating orientation. In this way, the scented material-holding portion 15 may be removable to, for example, change the particular scented material 17 that is used or clean the scented material-holding portion 15. In some embodiments, the scented material-holding portion 15 may be formed separately, as described, then optionally secured to the base structure lower portion 13 by way of, for example, an adhesive, a mechanical fastener, a press fit, firing the portions together (e.g., if the base structure 12 is made from ceramics), etc.

Figure 3:
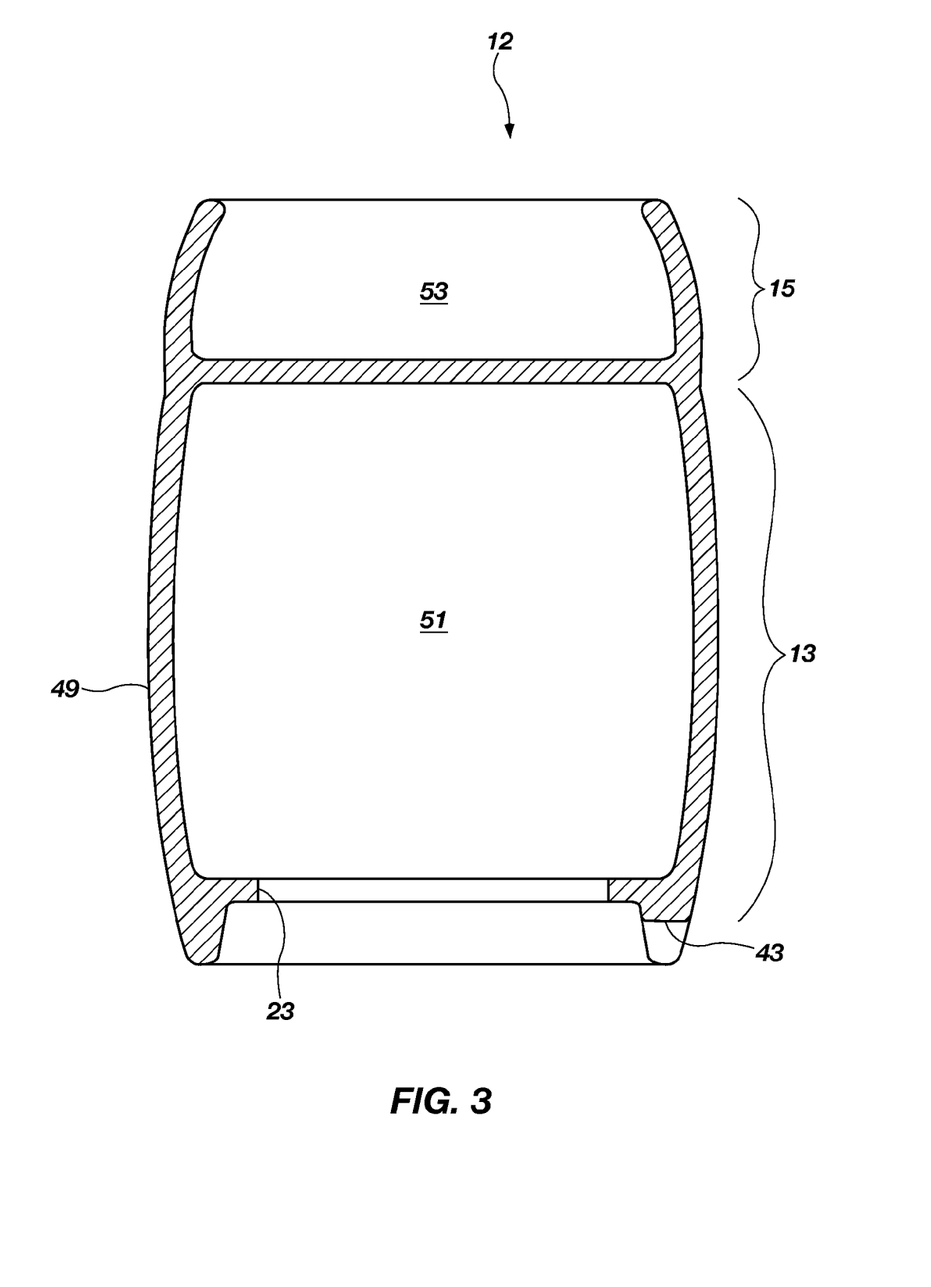
FIG. 3 is a cross-sectional side view of a base structure of a scent warmer according to another embodiment of the present invention.

FIG. 3 is a cross-sectional side view of base structure 12 of the scent warmer 11 according to another embodiment of the present invention. Similar elements between the base structures 12 of FIGS. 2 and 3 retain the same numerical designation for convenience despite some differences in structure, as will be apparent. Referring specifically to FIG. 3, in some embodiments, the base structure 12 may be formed of a base structure lower portion 13 and a scented material-holding portion 15 in a unitary construction. In other words, the base structure lower portion 13 and the scented material-holding portion 15 may be integrally formed of one continuous material. The base structure 12 may be formed in this manner to reduce costs in manufacture, to improve or adjust the aesthetics of the scent warmer 11, or for any other reason, as will be appreciated by one of ordinary skill in the art. In some embodiments, the unitary base structure 12 may include a lower opening 23 and optionally a recess 43, as described hereinabove.

In some embodiments, the sidewall 49 of the base structure lower portion 13 may be formed without holes 19 (FIG. 2) therethrough, as shown in FIG. 3. In such embodiments, the sidewall 49 or at least a portion thereof may comprise a material and structure that allows at least some light to pass therethrough. In other words, the sidewall 49 may exhibit less than 100% opacity to light within visible wavelengths. Or, in other words, at least a portion of the sidewall 49 may be at least somewhat translucent, or even transparent. The opacity of a surface or material may be a function of the type of material used and the geometry (e.g., thickness) of the surface formed. As used herein, the percentage of opacity refers to the percentage of visible light that is blocked from passing through a surface or material. Therefore, a material that exhibits 100% opacity blocks all visible light from passing therethrough and allows no visible light through the material. Similarly, a material or surface that exhibits 60% opacity blocks 60% of visible light and allows the remaining 40% of visible light to pass therethrough. The light that passes through a surface of less than 100% opacity may be, for example, diffused light; or, in other words, light may pass through the surface but features of objects or lights on the opposing side of the surface may be obscured or unclear to an observer. In some embodiments, the sidewall 49 may exhibit at most about 95% opacity. More particularly, some embodiments include a sidewall 49 that may exhibit at most about 90% opacity. Some embodiments include a sidewall 49 that may exhibit between about 20% opacity and 80% opacity. Yet other embodiments include a sidewall 49 that may exhibit between about 40% and 60% opacity. In other embodiments, a sidewall 49 of the base structure lower portion 13 may include areas of relatively higher opacity as compared to other areas of the sidewall 49. This may be accomplished by, for example, forming the sidewall 49 to have areas of varying thicknesses or of different materials. By way of non-limiting example, porcelain and glass are materials that may each exhibit a percentage of opacity as described.

In some embodiments, the scent warmer 11 may include a sidewall 49 that has both at least one hole 19 (FIG. 2) therethrough and at least a portion that includes a material having an opacity of less than 100%, as described hereinabove. Thus, some light may pass directly through the at least one hole 19 and some light may pass through a solid material of the sidewall 49, due to at least a portion of the sidewall 49 exhibiting less than 100% opacity.

Figure 4:
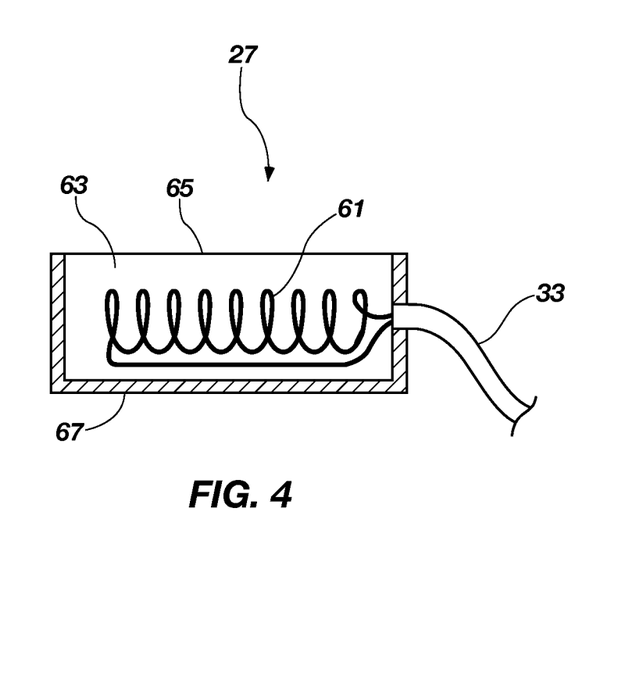
FIG. 4 is a partially cut-away view of an embodiment of the electrical heat source of the scent warmer of FIG. 1.

FIG. 4 is a partially cut-away view of an embodiment of an electrical heat source 27 of the scent warmer 11 of FIG. 1. By way of non-limiting example, the electrical heat source 27 may be a resistance heater. The electrical heat source 27 may include a coil 61 of resistive material that heats up as electricity is passed therethrough. The electrical heat source 27 may, optionally, include an encasing material 63 at least partially surrounding the coil 61. The encasing material 63 may protect the coil 61 from damage and provide a safety barrier for those who handle the electrical heat source 27. The encasing material 63 may also be configured to provide a surface 65 that may abut against another surface to be heated by the electrical heat source 27, such as, for example, a surface of a heat plate 25 (FIG. 1, and described in more detail hereinafter) or a bottom surface of the scented material-holding portion 15 (FIG. 1) to enhance heat transfer. The encasing material 63 may be formed of, by way of non-limiting example, a metal, a ceramic material, a polymer material, or a combination thereof.

Additionally, in some embodiments, the electrical heat source 27 may include a shell 67 at least partially surrounding the coil 61 and the encasing material 63 to enable safer handling, better heat transfer, structural integrity, and/or proper configuration of the electrical heat source 27. The shell 67 may be formed of, for example, at least one of a ceramic material, a metal material, and a polymer material. In some embodiments, the shell 67 may further include one or more features (not shown) to facilitate attachment to or coupling with the base structure 12 (FIGS. 1-3). For example, the shell 67 may include a recess or depression for positioning an end of the screw 35, as shown in FIG. 1. In some embodiments, the shell 67 may include a threaded portion to receive a screw the screw 35 or a bolt. In yet other embodiments, the shell 67 may include a hole therethrough for fastening the electrical heat source 27 to the base structure 12.

Although the coil 61 of resistive material is shown in FIG. 4 as a part of the electrical heat source 27, in some embodiments it is contemplated that the electrical heat source 27 may have, for example, other configurations, sizes, compositions, and lengths, as will be appreciated by one of ordinary skill in the art. By way of non-limiting example, the electrical heat source 27 may include two conductive posts (i.e., prongs) running parallel to each other through the encasing material 63. In such embodiments, the encasing material 63 may be selected to allow the passage of electricity from one post to the other post with some resistance, thereby producing heat. For example, the encasing material 63 may be a ceramic material. In some embodiments, the electrical heat source 27 may not be an incandescent light bulb. The electrical heat source 27, as described herein, may heat scented material 17 more efficiently than the prior art incandescent light bulb by being in closer proximity to the scented material 17 and by not losing as much energy in the form of visible light.

The electrical heat source 27 may be selected or designed to provide heat sufficient for heating a scented material 17 (FIG. 1) so that aroma dissipation is enhanced. For example, in some embodiments, the electrical heat source 27 may be capable of heating the scented material 17 to a temperature of at least about 45 degrees Celsius. More particularly, the electrical heat source 27 may be capable of heating the scented material 17 to a temperature of at least about 65 degrees Celsius. The heating capacity of the electrical heat source 27 may be chosen according to various factors, including, for example, the composition of the scented material 17, the melting point of the material (e.g., wax) used as the scented material 17, safety concerns or standards for electrical heaters, desired scent dissipation, etc.

Figure 5:
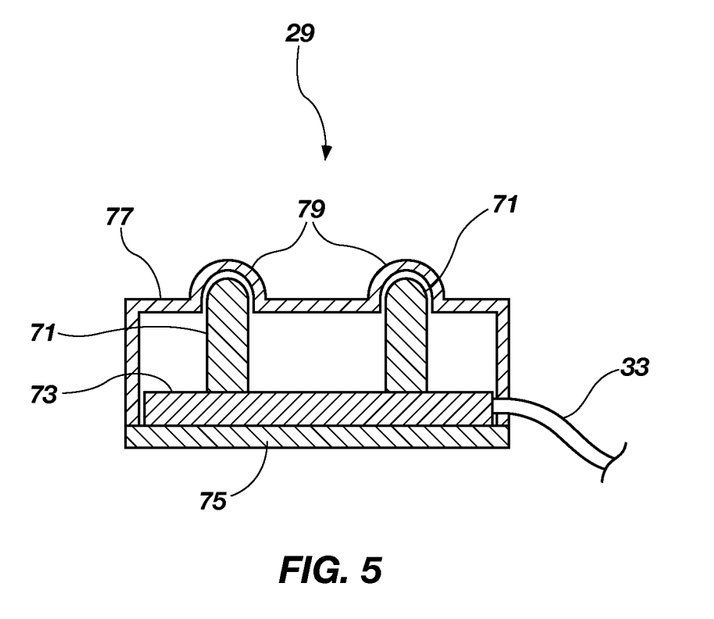
FIG. 5 is a cross-sectional side view of one embodiment of the filamentless light source of the scent warmer of FIG. 1.

FIG. 5 is a cross-sectional side view of one embodiment of the filamentless electrical light source 29 of the scent warmer 11 of FIG. 1. As used herein, the term "filamentless electrical light source" refers to any electrical light source that produces light in a way other than by heating a filament. By way of non-limiting example, a filamentless electrical light source may include one or more light-emitting diodes (LEDs), a compact fluorescent lamp (CFL), or any other light source that does not work by heating a filament. By way of further example, an incandescent light bulb is not a filamentless electrical light source, as the term is used herein.

In some embodiments, the filamentless electrical light source 29 may include at least one light-emitting diode (LED) 71 mounted on at least one printed circuit board (PCB) 73 with associated circuitry, as will be appreciated by one of ordinary skill in the art. In some embodiments, the at least one LED 71 may include a plurality of LEDs 71. Circuitry of the at least one PCB 73 may be configured to modify incoming electrical power into an appropriate power level and signal to operate the at least one LED 71. Optionally, the circuitry may cause the at least one LED 71 to flicker when electrical power is provided, to give the illusion of a flame. For example, flickering may be accomplished by the circuitry sequentially adjusting the electrical power to the at least one LED 71 to lower and higher power states so that the light intensity increases and decreases accordingly. The at least one PCB 73 and the at least one LED 71 may receive power through the electrical cord 33. In some embodiments, the at least one PCB 73 may not be necessary, in which case the at least one LED 71 receives power directly from a power supply without corresponding circuitry.

In some embodiments, the filamentless electrical light source 29 may also include a base plate 75 on which the at least one PCB 73 may be mounted, and a cover 77 at least substantially surrounding the at least one LED 71 and the at least one PCB 73. The cover 77 may include at least one at least partially transparent cover member 79 positioned over the at least one LED 71. The at least partially transparent cover member 79 may be at least substantially clear (i.e., it may allow at least substantially all visible light through), or it may be colored, for example. In this way, the color of the light emitting from the at least one LED 71 may be modified and determined by the at least partially transparent cover member 79. In other embodiments, the cover 77 may include holes through which a portion of the at least one LED 71 may protrude. In some embodiments, the color of the light may be determined by the color of the at least one LED 71 itself. By way of non-limiting example, the color of the light produced by the filamentless electrical light source 29 (controlled by the at least partially transparent cover member 79, the color of the at least one LED 71 itself, or a combination thereof) may be at least substantially white, red, orange, yellow, green, blue, purple, or any other desired color, or multiple colors.

In some embodiments, a plurality of LEDs 71 may each emit light of different wavelengths, the combination of which may produce a desired color for an overall effect. For example, a plurality of LEDs may include at least one red, green, and blue LED according to a red-green-blue (RGB) color scheme. For example, the circuitry may control the intensity of each of the plurality of LEDs such that different combinations of light may be produced to have a desired overall color or effect. In other embodiments, the LED 71 may be a multicolored LED that may emit light of different colors in response to a signal received from the circuitry. For example, a multi-colored LED may include red, green, and blue die in the same optical enclosure, which may be controlled and combined to render a desired color, in a similar manner as with a plurality of discrete LEDs of different colors. While RGB is a standard combination of primary colors in LEDs, other color combinations are within the scope of the present invention to combine and form a desired color. In summary, the LED 71 may be a single-colored LED, a cluster of smaller LEDs that lie underneath a single lens with the intensities of each LED in the cluster of smaller LEDs being controlled by the circuitry to produce an overall desired color, or the LED 71 may be a multi-colored LED that may be controlled by circuitry to produce an overall desired color or effect, or any other combination thereof configuration as would be apparent to one of ordinary skill in the art.

Although FIGS. 1 and 5 show the filamentless electrical light source 29 as comprising a pair of LEDs 71, other embodiments are contemplated, as well. For example, the filamentless electrical light source 29 may include only one LED 71. In other embodiments, the filamentless electrical light source 29 may include two or more LEDs 71 that may be of the same color as each other, or that may each produce different colors as each other. In addition, two or more LEDs may produce the same or different effects as each other.

In some embodiments, the filamentless electrical light source 29 may include a compact fluorescent lamp (CFL) (not shown). In such embodiments, the associated hardware may be different than that shown in FIG. 5 and described hereinabove. However, the CFL may provide light in a similar manner to that described and at a higher efficiency than a corresponding incandescent light bulb of the prior art, as described hereinabove. As with LEDs, color output from a CFL may be modified by the use of appropriately colored covers, or color of a sidewall 49 or portion thereof of base structure lower portion 13, by modifying a drive signal to one or more CFLs to generate a desired color, or combinations thereof.

Referring again specifically to FIG. 1, in some embodiments, the electrical components described hereinabove (e.g., the electrical heat source 27 and the filamentless electrical light source 29) may receive electrical power from a power supply connection 31 and through an electrical cord 33. The power supply connection 31 may include a plug (as shown in FIG. 1) configured for obtaining electricity from an electrical outlet. In some embodiments, the power supply connection 31 may comprise a compartment for a battery (not shown). In yet other embodiments, the power supply connection 31 may include both a plug and a battery compartment, such as in an embodiment that includes a plug and a backup battery capability. Furthermore, the electrical components of the scent warmer 11 may include a switch (not shown) to turn on power to the electrical heat source 27 and to the filamentless electrical light source 29. In additional embodiments (not shown), a plug may be rigidly attached to the base structure 12 such that the scent warmer 11 may be plugged directly into a wall outlet, with the weight of the scent warmer 11 supported by the plug and the wall outlet.

In some embodiments, the electrical components may further include at least one AC/DC converter, such as a rectifier (i.e., a component that changes electrical power from alternating current (AC) to direct current (DC)) or an inverter (i.e., a component that changes electrical power from direct current (DC) to alternating current (AC)) according to the power supply used and the methods by which the electrical heat source 27 and/or the filamentless electrical light source 29 operate.

Although FIG. 1 shows the electrical power flow going from a power supply connection 31 through input element 33 to the filamentless electrical light source 29 and then to the electrical heat source 27, other flows of electricity are contemplated. For example, in some embodiments, electricity may flow from the power supply connection 31 to the electrical heat source 27 first and then to the filamentless electrical light source 29. In some embodiments, electricity may flow from the power supply connection 31 to the electrical heat source 27 and to the filamentless electrical light source 29 in parallel (i.e., simultaneously). Furthermore, in some embodiments, additional circuitry and switches (not shown) may optionally be provided to control which elements receive power at a given time, to control the intensity of heat produced by the electrical heat source 27 or of light produced by the filamentless electrical light source 29, or a combination thereof.

With continued reference to FIG. 1, the electrical components of the scent warmer 11 described hereinabove may be at least partially disposed within a hollow portion of the base structure lower portion 13. In some embodiments, structural components may hold some of the various components in place. For example, the screw 35 may extend through a lower opening cover 39, a bracket 41, and the filamentless electrical light source 29 and may abut against the electrical heat source 27. At least one nut 37 may hold the screw 35 and the various components in place. In some embodiments, a lower opening cover 39, a bracket 41, the filamentless electrical light source 29, the electrical heat source 27, or any combination thereof may include a threaded portion complementary to the screw 35, such that the screw 35 may be engaged with the component or components described. Thus, the screw 35, lower opening cover 39, bracket 41, and nuts 37 may structurally hold the components in place at least partially within the base structure lower portion 13.

As shown in FIG. 1, the electrical heat source 27 may be positioned within the base structure lower portion 13 proximate the upper opening 21 such that the electrical heat source 27 may heat the scented material-holding portion 15. In some embodiments, the electrical light source 29 may be positioned within the base structure lower portion 13 at a distant location of the electrical heat source 27, such as proximate the lower opening 23 of the base structure lower portion 13. In some embodiments, the electrical light source 29 may be positioned within the base structure lower portion 13 at a location proximate the electrical heat source 27. As shown in FIG. 1, the screw 35 that structurally hold components in place may be a single screw that engages with both the electrical heat source 27 and the electrical light source 29. The screw 35 may extend from one end of the base structure lower portion 13 to the other end of the base structure lower portion 13. For embodiments that include the electrical light source 29 being positioned proximate the electrical heat source 27, the screw 35 may be shortened. Of course, the screw 35 being secured to both ends of the base structure lower portion 13 may provide additional stability to securing the electrical heat source 27 and the electrical light source 29. In some embodiments, a plurality of screws may be used to couple each of the electrical heat source 27 and the electrical light source 29 separately in place. For example, a first screw may engage with the electrical heat source 27, and a second screw may engage with the electrical light source 29.

In some embodiments, the scent warmer 11 includes a heat plate 25 under the scented material-holding portion 15. The heat plate 25 may be formed from a metal or metallic material. The electrical heat source 27 may be abutted against or coupled to a surface of the heat plate 25. By way of non-limiting examples, the electrical heat source 27 may be coupled to the heat plate 25 with adhesive, with a mechanical connection (e.g., a clip, screw, interference fit, etc.), by being pushed against the heat plate 25 with the screw 35 (as shown), or a combination thereof. In embodiments in which the scented material-holding portion 15 and the base structure lower portion 13 are separate and detachable, the heat plate may be attached to one of the scented material holding material-holding portion 15 or the base structure lower portion 13. For example, the heat plate 25 may be attached to the scented material-holding portion 15 and positioned such that the heat plate 25 abuts electrical heat source 27 if the scented material-holding portion 15 is coupled with the base structure lower portion 13 for operation.

In some embodiments, the scent warmer 11 may not include the heat plate 25. In such embodiments, the electrical heat source 27 may abut directly against a bottom of the scented material-holding portion 15 of the base structure 12, in the way described. This manner of connection (i.e., without the heat plate 25) may, for example, be used in the embodiment of the base structure 12 shown in FIG. 3.

While the present invetion has been described herein with respect to certain embodiments, those of ordinary skill in the art will recognize and appreciate that it is not so limited. Rather, many additions, additions, and modifications to the embodiments depicted and described herein may be made without departing from the scope of the invention as hereinafter claimed, and legal equivalents. In addition, features from one embodiment may be combined with features of another embodiment while still being encompassed within the scope of the invention as contemplated by the inventor. Further, the invention has utility in scent warmers having different designs and configurartions than those shown and described herein.

What is claimed is:

1. A scent warmer, comprising:
   a base structure, comprising:
      an at least substantially hollow lower portion having at least one sidewall; and
      a scented material-holding portion disposed over the at least substantially hollow lower portion;
   an electrical heat source disposed at least substantially within the at least substantially hollow lower portion and positioned proximate the scented material-holding portion;
   a filamentless electrical light source disposed at least substantially within the at least substantially hollow lower portion; and
   structural components sized and configured to hold the filamentless electrical light source and the electrical heat source in place within the at least substantially hollow lower portion, the structural components comprising:
      at least one screw extending approximately centrally through the at least substantially hollow lower portion of the base structure, wherein the at least one screw is engaged with both the filamentless electrical light source and the electrical heat source.

2. The scent warmer of claim 1, wherein the at least one sidewall comprises at least one hole therethrough configured to allow at least some light to pass therethrough.

3. The scent warmer of claim 1, wherein the at least a portion of the at least one sidewall comprises a material and structure exhibiting less than 100% opacity.

4. The scent warmer of claim 1, wherein the scented material-holding portion is removable from the at least substantially hollow lower portion.

5. The scent warmer of claim 1, further comprising a power supply input element configured and connected to provide power to the electrical heat source and the filamentless electrical light source.

6. The scent warmer of claim 5, further comprising circuitry configured to control at least one of flickering and intensity of light of the filamentless electrical light source.

7. The scent warmer of claim 1, further comprising a heat plate located between the scented material-holding portion and the electrical heat source.

8. The scent warmer of claim 1, wherein an end of the at least one screw abuts against the electrical heat source.

9. The scent warmer of claim 1 wherein the structural components further comprise:
at least one bracket coupled to the screw;
a lower opening cover through which the screw passes; and
at least one nut complementary to and engaged with the screw.

10. The scent warmer of claim 9, wherein at least one of the filamentless electrical light source, the electrical heat source, the lower opening cover, and the at least one bracket includes a threaded portion complementary to the at least one screw.

11. The scent warmer of claim 1, further comprising at least another screw engaged with the electrical light source.

12. The scent warmer of claim 1, wherein the scented material-holding portion and the at least substantially hollow lower portion are rigidly coupled together.

13. The scent warmer of claim 12, wherein the scented material-holding portion and the base structure lower portion comprise a unitary structure.

14. The scent warmer of claim 11, wherein the electrical heat source is positioned proximate the scented material-holding portion, and the filamentless electrical light source is positioned proximate an opposing end of at least substantially hollow lower portion.

15. A method of warming scented material, comprising:
coupling an electrical heat source disposed at least partially within a base structure with a plate having scented material disposed at least partially thereon, wherein coupling an electrical heat source with a plate comprises pushing the electrical heat source against the plate with a screw that extends approximately centrally through the base structure;
heating the plate having scented material disposed at least partially thereon by providing electrical power to the electrical heat source; and
producing light by providing electrical power to a filamentless electrical light source disposed at least partially within the base structure and engaged with the screw that extends approximately centrally through the base structure.

16. The method of claim 15, further comprising allowing at least some of the light produced by providing electrical power to a filamentless electrical light source to pass through the base structure.

17. The method of claim 16, wherein allowing at least some of the light to pass through the base structure comprises forming at least a portion of a sidewall of the base structure to comprise a material that exhibits less than 100% opacity.

18. The method of claim 16, wherein allowing at least some of the light to pass through the base structure comprises forming at least one hole in a sidewall of the base structure.

19. The method of claim 16, further comprising causing the light produced by providing electrical power to a filamentless electrical light source disposed at least partially within the base structure to vary in intensity.

20. A method of forming a scent warmer, comprising:
electrically connecting a power supply to a filamentless electrical light source and to an electrical heat source;
coupling the electrical heat source to a surface of a plate of a base structure, the electrical heat source disposed at least substantially inside a lower portion of the base structure;
disposing the filamentless electrical light source at least partially within the lower portion of the base structure;
engaging a centrally-located screw with both the electrical heat source and the filamentless electrical light source to hold the electrical heat source and the filamentless electrical light source in place relative to the base structure; and
disposing a scented material-holding portion proximate the electrical heat source.

21. The method of claim 20, wherein electrically connecting a power supply to a filamentless electrical light source comprises electrically connecting a power supply to at least one of a light-emitting diode (LED) and a compact fluorescent lamp (CFL).

22. The method of claim 20, further comprising forming at least one hole through the lower portion of the base structure.

23. The method of claim 20, further comprising selecting a material of at least a portion of the lower portion of the base structure to exhibit less than 100% opacity.

24. The method of claim 20, wherein coupling the electrical heat source to a surface of a plate of a base structure comprises coupling the electrical heat source to a surface of a heat plate comprising a metal or metallic material.

25. The method of claim 20, wherein coupling the electrical heat source to a surface of a plate of a base structure comprises coupling the electrical heat source to a surface of the scented material-holding portion of the base structure.

* * * * *